(12) United States Patent
Park et al.

(10) Patent No.: US 9,474,803 B2
(45) Date of Patent: Oct. 25, 2016

(54) COMPOSITION FOR STABILIZING FUSION PROTEIN IN WHICH PROTEIN AND FC DOMAIN ARE FUSED

(71) Applicant: ALTEOGEN INC., Daejeon (KR)

(72) Inventors: Soon Jae Park, Daejoen (KR); Seong-Kyu Kim, Daejeon (KR)

(73) Assignee: ALTEOGEN INC., Daejeon (KR)

( * ) Notice: Subject to any disclaimer, the term of this patent is extended or adjusted under 35 U.S.C. 154(b) by 0 days.

(21) Appl. No.: 14/439,644

(22) PCT Filed: Oct. 23, 2013

(86) PCT No.: PCT/KR2013/009474
§ 371 (c)(1),
(2) Date: Apr. 29, 2015

(87) PCT Pub. No.: WO2014/084508
PCT Pub. Date: Jun. 5, 2014

(65) Prior Publication Data
US 2015/0313996 A1 Nov. 5, 2015

(30) Foreign Application Priority Data
Nov. 27, 2012 (KR) .................. 10-2012-0134946

(51) Int. Cl.
*A61K 39/00* (2006.01)
*A61K 39/395* (2006.01)
*A61K 47/02* (2006.01)
*C07K 14/705* (2006.01)
*C01C 1/16* (2006.01)
*C09K 15/20* (2006.01)
*A61K 38/17* (2006.01)
*A61K 47/26* (2006.01)
*A61K 9/08* (2006.01)

(52) U.S. Cl.
CPC .............. *A61K 47/02* (2013.01); *A61K 9/08* (2013.01); *A61K 38/1793* (2013.01); *A61K 47/26* (2013.01); *C01C 1/164* (2013.01); *C07K 14/70578* (2013.01); *C09K 15/20* (2013.01); *C07K 2319/30* (2013.01)

(58) Field of Classification Search
None
See application file for complete search history.

(56) References Cited

U.S. PATENT DOCUMENTS

| 4,362,661 | A | 12/1982 | Ono et al. |
| 5,821,337 | A | 10/1998 | Carter et al. |
| 5,945,098 | A | 8/1999 | Sarno et al. |
| 7,648,702 | B2 | 1/2010 | Gombotz et al. |
| 8,216,575 | B2* | 7/2012 | Yu ................. C07K 14/71 424/134.1 |
| 9,168,286 | B2* | 10/2015 | Chevrier .......... C07K 14/70575 |
| 2007/0036806 | A1 | 2/2007 | Glaesner et al. |
| 2007/0092940 | A1 | 4/2007 | Eigenbrot et al. |
| 2010/0143368 | A1 | 6/2010 | King et al. |
| 2010/0254985 | A1 | 10/2010 | Allan et al. |
| 2011/0280891 | A1 | 11/2011 | Liu et al. |
| 2012/0116057 | A1 | 5/2012 | Kannan et al. |
| 2014/0255400 | A1* | 9/2014 | Maloney ............ A61K 38/1793 424/134.1 |

FOREIGN PATENT DOCUMENTS

| JP | 2005-500304 A | 1/2005 |
| JP | 2005-527503 A | 9/2005 |
| JP | 2007-521315 A | 8/2007 |
| JP | 2011-500757 A | 1/2011 |
| JP | 2012-519706 A | 8/2012 |
| KR | 1020080094781 A | 10/2008 |
| WO | 9426295 A1 | 11/1994 |
| WO | 03000014 A2 | 1/2003 |
| WO | 03072060 A2 | 9/2003 |
| WO | 2005012353 A1 | 2/2005 |
| WO | 2008147143 A2 | 12/2008 |
| WO | 2009053360 A1 | 4/2009 |
| WO | 2010102241 A1 | 9/2010 |
| WO | 2011141926 A2 | 11/2011 |
| WO | 2012143418 A1 | 10/2012 |
| WO | 2013006454 A1 | 1/2013 |

OTHER PUBLICATIONS

Chi et al. 2003. Pharm Res. 20:1325-36.*
Andya, J., et al., "Chapter 13: Analysis of Irreversible Aggregation, Reversible Self-association and Fragmentation of Monoclonal Antibodies by Analytical Ultracentrifugation", "Current Trends in Monoclonal Antibody Development and Manufacturing Biotechnology: Pharmaceutical Aspects", Oct. 10, 2009, pp. 207-227, vol. XI, Publisher: Springer, Published in: New York.
Chung, H., et al., "The N-terminal alanine-extended GLP-1/IgG-Fc fusion protein confers resistance to DPP-IV and reduces serum glucose level in db/db mice", "Regulatory Peptides", May 27, 2011, pp. 1-3, vol. 170.
Hamada, H., et al., "Effect of Additives on Protein Aggregation", "Current Pharmaceutical Biotechnology", Jun. 2009, pp. 400-407, vol. 10.

(Continued)

*Primary Examiner* — Shulamith H Shafer
(74) *Attorney, Agent, or Firm* — Hultquist, PLLC; Steven J. Hultquist (57) ABSTRACT

The present invention relates to a composition for stabilizing a fusion protein of a physiologically active protein and an Fc domain, and more particularly to a method of stabilizing a fusion protein of a protein and an Fc domain using a composition containing an ammonium salt or a combination of an ammonium salt and succinate. The composition containing an ammonium salt or a combination of an ammonium salt and succinate according to the present invention can effectively inhibit the aggregation of the protein-Fc domain fusion protein, and thus enables the fusion protein to be stored for a long period of time. Accordingly, the composition can be widely used in the medical field that uses the protein-Fc domain fusion protein.

7 Claims, 8 Drawing Sheets

(56) References Cited

OTHER PUBLICATIONS

Harn, N., et al., "Chapter 14: Biophysical Signatures of Monoclonal Antibodies", "Current Trends in Monoclonal Antibody Development and Manufacturing Biotechnology: Pharmaceutical Aspects", Oct. 10, 2009, pp. 229-246, vol. XI, Publisher: Springer, Published in: New York.

Kunz, W., et al., "Zur Lehre von der Wirkung der Salze (about the science of the effect of salts): Franz Hofmeisters historical papers", "Current Opinion in Colloid and Interface Science", Aug. 2004, pp. 19-37, vol. 9.

Philo, J., et al., "Mechanisms of Protein Aggregation", "Current Pharmaceutical Biotechnology", Jun. 2009, pp. 348-351, vol. 10.

Shire, S., et al., "Chapter 9: Challenges in the Development of High Protein Concentration Formulations", "Current Trends in Monoclonal Antibody Development and Manufacturing Biotechnology: Pharmaceutical Aspects", Oct. 10, 2009, pp. 131-147, vol. XI, Publisher: Springer, Published in: New York.

* cited by examiner

COMPOSITION FOR STABILIZING FUSION PROTEIN IN WHICH PROTEIN AND FC DOMAIN ARE FUSED

CROSS-REFERENCE TO RELATED APPLICATIONS

This application is a U.S. national phase under the provisions of 35 U.S.C. §371 of International Patent Application No. PCT/KR13/09474 filed Oct. 23, 2013, which in turn claims priority of Korean Patent Application No. 10-2012-0134946 filed Nov. 27, 2012. The disclosures of such international patent application and Korean priority patent application are hereby incorporated herein by reference in their respective entireties, for all purposes.

TECHNICAL FIELD

The present invention relates to a composition for stabilizing a fusion protein of a physiologically active protein and an Fc domain, and more particularly to a method of stabilizing a fusion protein of a protein and an Fc domain using a composition containing an ammonium salt or a combination of an ammonium salt and succinate.

BACKGROUND ART

Antibody drugs that are used for the purpose of treating diseases are biodrugs to which advanced bioprocess technologies, including cell line development technology, cell culture technology and purification technology, are applied. As these antibody drugs have been proven to have excellent efficacy and safety compared to existing drugs, the demand therefor has increased day by day. For example, a fusion protein (TNFR:Fc; etanercept) prepared by fusing the extracellular ligand-binding portion of human p75 human tumor necrosis factor receptor to the Fc domain of human IgG1 has been used as an agent for treating rheumatoid arthritis. In addition, in order to increase the in vivo half-life of physiologically active substances, there was an attempt to develop a diabetes therapeutic agent using a fusion protein of a GLP-1R agonist and an Fc domain (US2004-0558627; Chung, H. S. et al., *Regulatory peptide*, 170, 2011). In addition, there was an attempt to fuse a physiologically active substance such as hGH or EPO to an Fc domain in order to increase the in vivo half-life of the physiologically active substance (KR10-2008-7018012). In recent years, a fusion protein (aflibercept) of a VEGF receptor and an Fc domain has been approved and used as an agent for treating wet age-related macular degeneration (WAMD).

However, the fusion proteins as described above have problems in that they have a large and complex structure and are physically unstable, thus causing aggregation. Various factors that cause such aggregation are present in processes of producing and storing proteins.

For example, aggregation may be caused by one or more of the following factors. During purification, pH, the kind of salt, salt concentration, temperature, contact with air, stirring speed and the like, which are not optimal, may cause aggregation, and during formulation, conditions for concentration of proteins may cause aggregation. During the exchange of buffer, passing through a filter, stirring and the like may cause aggregation, and during storage, a change in temperature, a change in pH, contact with air, stirring and the like may cause aggregation. In addition, when a formulation containing a protein is exposed to light, aggregation may also occur, and the material of a package may also cause aggregation (Hamada, H. et al., *Current Pharmaceutical Biotechnology*, 10:400, 2009).

The most major aggregation of fusion proteins in buffer occurs when the hydrophobic regions of the antibody protein are exposed due to the structural change thereof. In other words, the hydrophobic regions of protein molecules are gathered together to form an aggregation, and this aggregation may also occur in an irreversible manner due to the formation of covalent bonds between antibody proteins (Hamada, H. et al., *Current Pharmaceutical Biotechnology*, 10:348, 2009).

Fusion proteins or antibody proteins that aggregated for the above-described reasons generally have reduced activity or lose their activity with the passage of time. In addition, when these proteins aggregate, they have antigenicity that does not appear in a non-aggregated state, and thus can cause the production of antidrug antibody (ADA) when they are injected into the human body. Therefore, there is an urgent need for a method for reducing the aggregation of fusion proteins and a stabilized formulation comprising a fusion protein that exhibits a reduced level of aggregation (Current Trends in Monoclonal Antibody Development and Manufacturing, Biotechnology: Pharmaceutical Aspects Volume XI, 2010, pp 271-291).

For this purpose, a method of either adding an excipient for preventing aggregation or controlling pH or a buffer composition was attempted. In the case in which the hydrophobic groups of an antibody protein are exposed to the surface of the protein molecules and bonded to each other to cause aggregation, an excipient capable of stabilizing the exposed hydrophobic groups is used to prevent the aggregation. For example, there are reports on the use of amino acids such as arginine, lysine, proline, histidine and glycine (U.S. Pat. No. 4,362,661A and U.S. Pat. No. 7,648,702), polysorbate-based surfactants, amphiphilic polymers such as polyethylene glycol (PEG) or polyvinyl pyrrolidone (PVP), polysaccharides such as dextran, or monosaccharides or disaccharides such as sucrose, maltose or trehalose (U.S. Pat. No. 5,945,098A).

However, a fusion protein of a protein and an Fc domain is less stable than generally produced antibody proteins, and thus shows a stronger tendency to form an aggregation compared to other proteins or antibody proteins. There is an example in which a formulation was prepared by adding a surfactant such as polysorbate to the protein-Fc domain fusion protein in order to prevent the aggregation of the fusion protein (Steven J. Shire et al., *Biotechnology: Pharmaceutical Aspects*, Current Trends in Monoclonal Antibody Development and Manufacturing, XI:115, 2010).

Accordingly, the present inventors have found that a composition containing an ammonium salt or a combination of an ammonium salt and succinate can increase the stability of a fusion protein of a protein and an Fc domain by inhibiting the aggregation of the fusion protein so that it can be easily stored for a long period of time, thereby completing the present invention.

DISCLOSURE OF INVENTION

Technical Problem

It is an object of the present invention to provide a composition for stabilization that can increase the stability of a fusion protein of a physiologically active protein and an Fc domain by inhibiting the aggregation of the fusion protein, and a method of stabilizing the protein-Fc domain fusion protein using the composition.

Another object of the present invention is to provide a composition for preventing and treating disease, which comprises the composition for stabilization.

Technical Solution

To achieve the above objects, in one aspect, the present invention provides a composition for stabilizing a protein-Fc domain fusion protein, which contains an ammonium salt or a combination of an ammonium salt and succinate, and a composition for preventing and treating disease, which comprises the composition for stabilizing the fusion protein.

In another aspect, the present invention provides a method of stabilizing a protein-Fc domain fusion protein by adding an ammonium salt or a combination of an ammonium salt and succinate to a composition containing the fusion protein.

BRIEF DESCRIPTION OF THE DRAWINGS

Arg: arginine; AmCl: ammonium chloride; AmSul: ammonium sulfate; Am+Lys: ammonium chloride+lysine; Am+EDTA: ammonium chloride+EDTA; Am+Polysorabate 20: ammonium chloride+polysorbate 20; Am+Sucrose: ammonium chloride+sucrose.

Arg: arginine; AmCl#: ammonium chloride # %; AmSul: ammonium sulfate; Am #+Lys: ammonium chloride #%+lysine; Am #+Suc: ammonium chloride #%+sucrose.

Enbrel: commercially available etanercept (Enbrel) formulation.

AmCl: ammonium chloride; AmCl+Lys: ammonium chloride+lysine.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

As used herein, "a fusion protein of a protein and an Fc domain" or "a protein-Fc domain fusion protein" means a fusion protein comprising a protein fused to an Fc domain that is an antibody constant region, in which the protein means an amino acid polymer made up of several amino acids formed by peptide bonds. Also, a polypeptide has the same meaning as an oligopeptide having a low molecular weight and a protein having a high molecular weight. Thus, as used herein, "a fusion protein of a protein and an Fc domain" has the same meaning as "a fusion protein of a polypeptide and an Fc domain".

In the present invention, "protein" is a protein or polypeptide exhibiting any physiological activity, and the kind thereof is not limited. Preferably, the protein that is used in the present invention may be selected from the soluble portions of various receptors such as TNF-receptor and VEGF receptor, GLP-1 analogs and derivatives, flt3 ligand, CD40 ligand, erythropoietin, thrombopoietin, calcitonin, Fas ligand, receptor activator of NF-kappa B ligand (RANKL), TNF-related apoptosis-inducing ligand (TRAIL), thymic stroma-derived lymphopoietin, granulocyte growth stimulating glycoprotein, granulocyte/macrophage growth stimulating glycoprotein, mast cell growth factor, stem cell growth factor, epidermal growth factor, RANTES, growth hormone, insulin, insulinotropin, insulin-like growth factors, parathyroid hormone, interferons, nerve growth factors, glucagon, interleukins 1~18, colony stimulating factors, lymphotoxin-β, tumor necrosis factor (TNF), leukemia inhibitory factor, oncostatin-M, and various ligands for cell surface molecules Elk and Hek (such as the ligands for eph-related kinases, or LERKS). Most preferably, it may be the extracellular ligand binding domain of human p75 TNF receptor.

As used herein, "soluble portion of receptor" means an extracellular ligand-binding domain, or a region comprising an extracellular ligand-binding domain and a transmembrane domain.

In the present invention, "Fc domain" means the constant domain of an antibody. It is preferably the Fc domain of human IgG1, but is not limited thereto. In addition to human IgG1, IgG2, IgG3 and IgG4 may also be used, and the Fc domain may comprise part or all of the CH1 domain, CH2 domain, CH3 domain and hinge region of IgG1, IgG2, IgG3 and IgG4. Preferably, it may comprise the CH2 domain, the CH3 domain and the hinge region, excluding the CH1 domain.

The protein-Fc domain fusion protein in the present invention may be produced according to a general method known in the art. When the fusion protein is produced in cells, materials other than the fusion protein may be removed by one or more processes selected from among centrifugation, ultrafiltration and/or chromatography processes.

In one aspect, the present invention is directed to a composition for stabilizing a protein-Fc domain fusion protein, which contains an ammonium salt.

"Ammonium salt" in the present invention means a salt produced by the reaction of ammonia and acid, and may be represented by the formula $NH_4X$ (X=monovalent acid group). Preferably, it may be selected from among ammonium chloride, ammonium sulfate, ammonium carbonate, and ammonium nitrate, but is not limited thereto.

Various kinds of salts change the solubility of proteins (Kunz, W. et al., *Curr. Opin. Coll. Interface Sci.*, 9:1937, 2004), and the solubility of proteins is associated with an increase in the surface tension. A cation, which maximizes surface tension and increases the stability of proteins, is $NH_4^+$. However, the use of an ammonium salt to inhibit the aggregation of a fusion protein or stabilize a composition containing a fusion protein has not yet been reported. The present inventors have found that, when a fusion protein of a protein and an Fc domain is stored in an aqueous solution containing an ammonium salt, the aggregation of the fusion protein is effectively inhibited. Thus, the present invention provides a composition for stabilizing a fusion protein of a protein and an Fc domain, the composition containing an ammonium salt.

Figure 1:
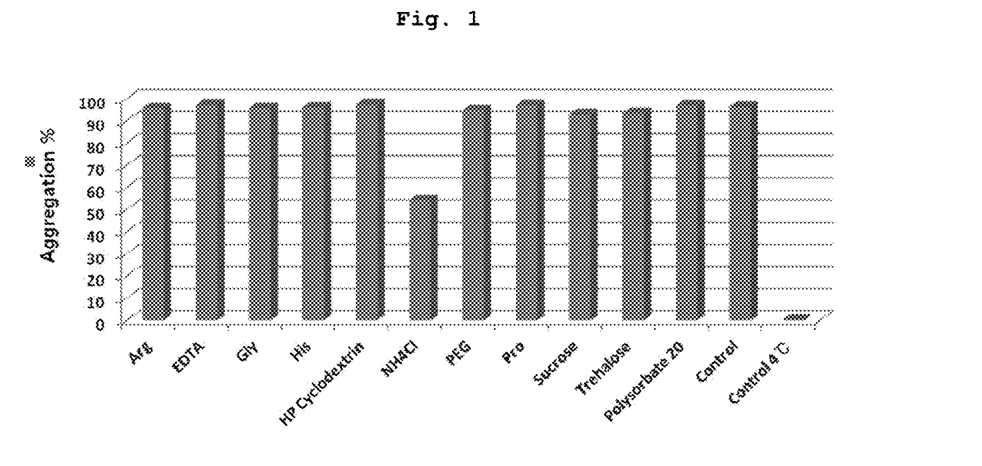
FIG. 1 shows the results of measuring the aggregation degree of etanercept (a fusion protein of the water-soluble portion of TNF receptor and an Fc domain) after storing Etanercept in formulation solutions containing various kinds of excipients (arginine (Arg), EDTA, glycine (Gly), histidine (His), hydroxypropyl cyclodextrin (HP Cyclodextrin), ammonium chloride, polyethylene glycol (PEG), proline (Pro), sucrose, trehalose and polysorbate 20) at 50° C. for 1 week.
Figure 2:
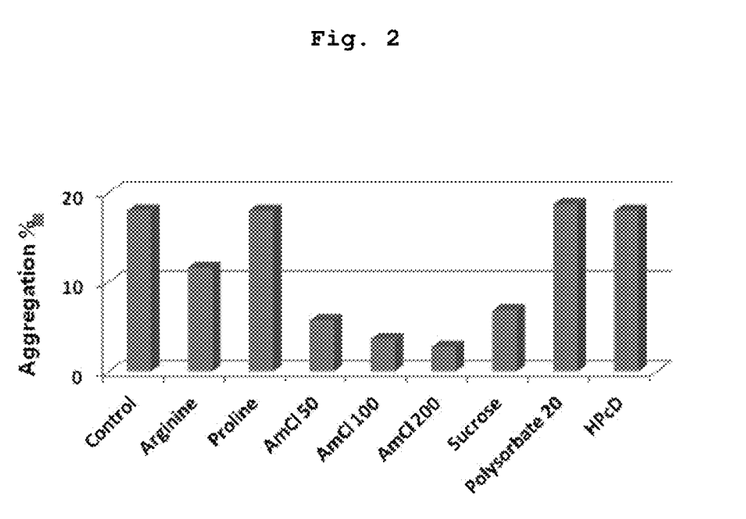
FIG. 2 shows the results of measuring the aggregation degree of etanercept after storing etanercept in formulation solutions containing various kinds of excipients (arginine (Arg), proline (Pro), 50 mM ammonium chloride, 100 mM ammonium chloride, 200 mM ammonium chloride, sucrose, polysorbate 20, and hydroxypropyl cyclodextrin (HPcD)) at 50° C. for 1 week.

As an ammonium salt that is used in the present invention, one selected from among ammonium chloride, ammonium sulfate, ammonium carbonate, and ammonium nitrate may be contained at a concentration of 5-500 mM. In an example of the present invention, an ammonium salt was used at a concentration of 12.5-200 mM, but even when an ammonium salt is used at a concentration of 12.5 mM or lower or at a concentration of 200 mM or higher, it exhibits the effect of inhibiting the aggregation of the fusion protein. Thus, the ammonium salt in the present invention effectively inhibits the aggregation of a fusion protein of a polypeptide and an Fc domain. In another example of the present invention, it was shown that, when a fusion protein comprising the extracellular ligand binding domain of human p75 tumor necrosis factor receptor fused to the Fc domain of human IgG1 was stored in an ammonium salt or ammonium sulfate solution, the aggregation degree of the fusion protein decreased by up to about 80% compared to the fusion protein that was not stored in an ammonium salt solution (FIGS. 1 and 2).

In another aspect, the composition for stabilizing the protein-Fc domain fusion protein according to the present invention may further comprise succinate. Succinate in the composition functions as a buffer that further reduces the aggregation of the protein-Fc domain fusion protein by controlling the pH of the composition containing the protein-Fc domain fusion protein.

The succinate is added to a concentration of 5-200 mM, and more preferably 20-30 mM. Not only sodium succinate, but also various succinates known in the art may be used in the present invention. In the composition containing succinate, the succinate buffer controls the pH of the composition to 5.5-6.5, preferably 6.0-6.3. If the pH of the composition is lower than 5.5 or higher than 6.5, the aggregation of the fusion protein will increase, and for this reason, the pH is preferably controlled in the above range.

Figure 6:
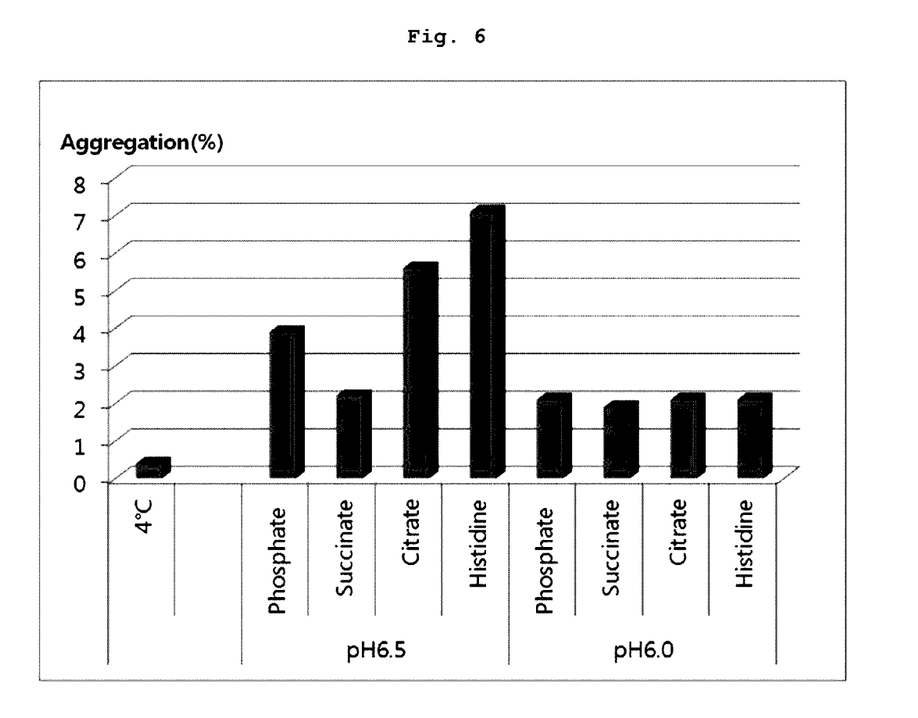
FIG. 6 shows the results of measuring the aggregation degree of etanercept after storing etanercept in various kinds of buffers (sodium phosphate, sodium succinate, sodium citrate, and histidine) containing ammonium chloride at 45° C. for 5 days.
Figure 7:
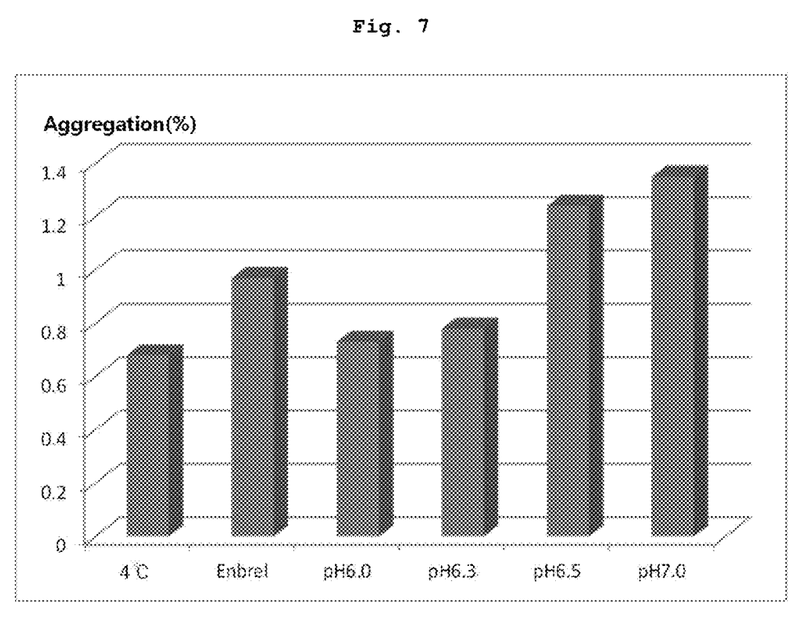
FIG. 7 shows the results of measuring the aggregation degree of etanercept after storing etanercept in sodium succinate buffer compositions containing ammonium chloride at varying pHs and 45° C. for 5 days.

In an example of the present invention, each of sodium phosphate, sodium succinate, sodium citrate and histidine buffers was added to an ammonium chloride excipient proven to have the effect of inhibiting the aggregation of the fusion protein in order to examine the difference in protein aggregation inhibitory effect between the buffers. As a result, it was shown that aggregation was significantly lower in a formulation containing sodium succinate as a buffer than in a commercially available etanercept (Enbrel™) formulation containing sodium phosphate as a buffer at pH 6.5. Also, it could be seen that a formulation containing sodium succinate exhibited an excellent aggregation inhibitory effect compared to formulations containing other buffers at pH 6.0 (FIG. 6). In addition, the aggregation inhibitory effect of sodium succinate buffer was examined at various pH in order to maximize the effect thereof, and as a result, it could be seen that, as the pH of sodium succinate decreased, aggregation was lower, and that aggregation was significantly lower than that of a commercially available etanercept formulation (comparative formulation) at pH 6.0 and pH 6.3 (FIG. 7).

Meanwhile, amino acids are known to inhibit the aggregation of proteins, and among them, basic amino acids have excellent effects on the prevention of aggregation. In the case of etanercept that is an agent for treating rheumatoid arthritis, an arginine is used as an anti-aggregation agent (U.S. Pat. No. 7,648,702 B2), and a formulation for stabilizing an Fc-modified antibody, which comprises a combination of lysine, arginine, histidine, saccharide, acidic buffer and polysorbate, was reported (US 2010-0254985). In addition, the use of saccharides such as trehalose, sucrose, mannitol or maltose, or anionic buffers such as phosphate or citrate was reported. Also, a surfactant can adhere to the exposed hydrophobic regions of proteins and increase the solubility of the proteins to thereby prevent the aggregation of the proteins, and thus polysorbate is typically used in antibody protein formulations such as Muromonab, Abciximab, Rituximab, Daclizimab, Alemtuzumab, Adalimumab, Bevacizumab, and Natalizumab.

Thus, the composition for stabilizing the protein-Fc domain fusion protein according to the present invention may further contain one or more excipients selected from among basic amino acids, saccharides and surfactants in order to further reduce the aggregation of the fusion protein.

As a basic amino acid, arginine, lysine, histidine or the like may be used at a concentration of 1-50 mM, and as a saccharide, sucrose, trehalose, mannitol, maltose or the like may be used as a concentration of 0.5-10% w/v, and as a surfactant, Triton, Tween or Pluronic series may be used at a concentration of 0.001-0.1% w/v, but are not limited. Any excipient may be used in the present invention without limitation, as long as it may be used in the art to inhibit the fusion proteins or antibody proteins.

Figure 8:
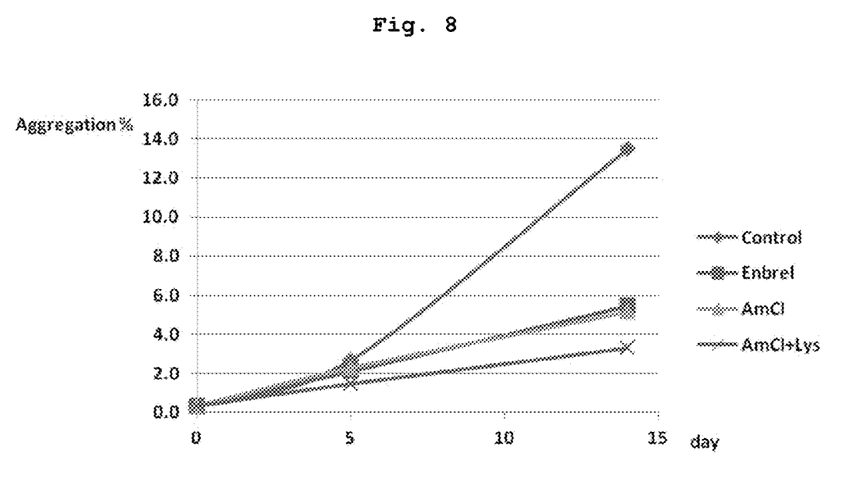
FIG. 8 shows the results of measuring the aggregation degree of Etanercept after storing Etanercept in sodium succinate buffer compositions containing ammonium chloride and lysine at 45° C. for 14 days.

In an example of the present invention, the aggregation inhibitory effect of a combination of a sodium succinate buffer, an ammonium ion component and a basic amino acid was examined, and as a result, it was shown that the degree of aggregation was significantly lower in a composition containing ammonium chloride, succinate and lysine than in an etanercept formulation (comparative formulation) (FIG. 8).

In another aspect, the present invention is directed to a method of stabilizing a protein-Fc domain fusion protein by adding an ammonium salt to a composition containing the fusion protein. The composition may further contain succinate. Succinate may be contained at a concentration of 5-200 Mm in the form of a buffer having a pH of 5.5-6.5.

In an example of the present invention, as the protein-Fc domain fusion protein, the commercially available arthritis therapeutic agent etanercept and a protein product obtained by expressing a protein in CHO cells and purifying the expressed protein were used. In order to examine whether the ammonium salt according to the present invention inhibits the aggregation of the fusion protein and is effective in stabilizing a formulation containing the fusion protein, an experiment was performed, and as a result, it could be seen that the use of the ammonium salt according to the present invention exhibited a better effect on the inhibition of aggregation of the fusion protein compared to arginine that is used to prevent the aggregation of the etanercept product (Example 2).

Therefore, in a preferred embodiment, the present invention provides a composition for treating arthritis, which contains an ammonium salt and a fusion protein comprising the extracellular ligand binding domain of human p75 tumor necrosis factor receptor fused to the Fc domain of human IgG1.

EXAMPLES

Hereinafter, the present invention will be described in further detail with reference to examples. It will be obvious to a person having ordinary skill in the art that these examples are illustrative purposes only and are not to be construed to limit or change the scope of the present invention.

Example 1

An experiment was performed using etanercept protein as a fusion protein of a protein and an Fc domain. As used herein, "TNFR:Fc" means etanercept protein, and "TNFR:Fc formulation" means a formulation containing etanercept protein.

The experiment in this Example was performed to compare the effects of excipients that inhibit the aggregation of TNFR:Fc. Specifically, the experiment was performed to examine whether the aggregation of TNFR:Fc at 50° C. differs between excipients. A solution having the same formulation as used in the Enbrel product (Amgen, USA), except for arginine, was prepared, and each excipient was added thereto. The prepared aqueous solutions (25 mg/ml etanercept, 0.66% w/v sucrose, 65 mM sodium chloride, 17 mM sodium phosphate, pH 6.4) were stored at 50° C., and then the degree of aggregation was compared between the aqueous solutions. The final concentrations of excipients in the aqueous solutions were 25 mM arginine, 100 mM proline, 80 mM histidine, 100 mM glycine, 0.2 M ammonium chloride, 10 mM EDTA, 20% w/v sucrose, 20% w/v trehalose, 10% w/v polyethylene glycol, 0.04% w/v polysorbate 20 (Tween 20), and 0.1% w/v hydroxypropyl cyclodextrin, and the aggregation degree of TNFR:Fc was measured using SE-HPLC. The protein was injected into a TSK-gel G3000SWXL (7.8×300 mm) HPLC column (TOSOH, Japan) under the buffer mobile phase conditions of 50 mM sodium phosphate (pH 6.8), 0.15M sodium chloride and 0.05% w/v sodium azide, and then the peak of the protein at 280 nm was detected. The aggregate of TNFR:Fc was eluted from the column earlier than the main peak, and the aggregation degree was calculated by comparing the peak area of the aggregate with the area of the main peak.

The results of storage at 50° C. for 1 week indicated that the aggregation of TNFR:Fc protein did significantly differ between the excipients. The protein (a control without an anti-aggregation excipient) stored at 4° C. (cold storage temperature) showed little or no aggregation, whereas most of the protein did aggregate 50° C. regardless of the kind of excipient (FIG. 1). Among them, the surfactant polysorbate 20, hydroxypropyl cyclodextrin, the amphiphilic polymer polyethylene glycol, the metal ion removing agent EDTA, and the amino acid excipients (arginine, proline, histidine, glycine, etc.) did not inhibit the aggregation of the protein (FIG. 1). However, sucrose and trehalose, which are saccharide excipients, showed slightly better effects on the prevention of aggregation compared to other excipients. In addition, in the case of other excipients, whereas when ammonium chloride was used as an excipient, only about 50% of the protein did aggregate.

From the above results, it could be seen that the aggregation of TNFR:Fc under severe conditions was effectively inhibited by the use of an ammonium use.

Example 2

An experiment was performed using TNFR:Fc as a protein-Fc domain fusion protein. The experiment was performed to compare the degree of aggregation between the use of the excipient arginine that is used to inhibit the aggregation of TNFR:Fc, and the use of other excipients.

Excipients selected for comparison were proline, sodium chloride, sucrose, polysorbate 20 and hydroxypropyl cyclodextrin. An arginine-free negative control and a 25 mM arginine-containing positive control, which contain final concentration with 10 mg/ml TNFR:Fc, 1% w/v sucrose, 100 mM sodium chloride, 25 mM sodium phosphate (pH 6.4), were prepared. In addition, formulations obtained by adding each of 100 mM proline, 50-200 mM ammonium chloride, 20% w/v sucrose, 0.04% w/v polysorbate 20 and 0.1% w/v hydroxypropyl cyclodextrin were tested. Each of the formulations was stored at 50° C. for 1 week in the same manner as described in Example 1. Aggregation was examined using SE-HPLC in the same manner as described in Example 1.

TNFR:Fc was stored at 50° C. for 1 week, and as a result, the formulation containing arginine showed an aggregation degree of about 10% (FIG. 2). However, it could be seen that the other amine acid proline showed an insignificant effect on the prevention of aggregation, and polysorbate 20 and hydroxypropyl cyclodextrin (HPCD) which are frequently used as anti-aggregation agents in antibody protein formulations had little or no effects on the prevention of aggregation. However, sucrose that is a typical protein stabilizer showed an excellent effect on the prevention of aggregation compared to arginine when it was added in an excessive amount (20% w/v). It could be seen that the anti-aggregation effect of ammonium chloride that showed an excellent stabilization effect in Example 1 increased as the concentration thereof increased (see FIG. 2). In addition, it could be seen that the use of 50 mM ammonium chloride showed a better effect on the inhibition of aggregation compared to the use of 25 mM arginine.

Example 3

In this Example, in order to further prove the aggregation inhibitory effect of the ammonium chloride excipient proven to have an aggregation inhibitory effect at high temperature, an experiment was performed at a temperature of 37° C. The experiment was performed to prove the aggregation inhibitory effect of ammonium sulfate as another ammonium salt and a combination of other excipients generally known to have the ability to inhibit protein aggregation. Specifically, each excipient was added to a stabilization buffer containing 25 mg/ml TNFR:Fc, 1% w/v sucrose, 100 mM sodium chloride and 25 mM sodium phosphate (pH 6.4), and then each buffer was stored at 37° C. for 4 weeks, followed by measurement.

A stabilization buffer composition containing no excipient for aggregation inhibition (negative control formulation), a formulation containing 25 mM arginine (positive control formulation), a formulation containing 50 mM ammonium chloride, a formulation containing 25 mM ammonium sulfate, a formulation containing 50 mM ammonium chloride and 1 mM EDTA, a formulation containing 50 mM ammonium chloride and 0.1% w/v polysorbate 20, a formulation containing 50 mM ammonium chloride and 5% w/v sucrose, and a formulation containing 50 mM ammonium chloride and 25 mM lysine were used. Each of the formulations was stored at 37° C. for 4 weeks. The effect of inhibiting aggregation was measured using SE-HPLC in the same manner as described in Example 1.

TABLE 1

Results of measuring the aggregation of etanercept after storing etanercept in ammonium chloride-containing formulations at 37° C. for 4 weeks
% Aggregation

| | week | | | |
|---|---|---|---|---|
| | 0 | 1 | 2 | 4 |
| Control | 0.3 | 1.3 | 1.4 | 3.1 |
| Arg | | 1.1 | 1.3 | 2.7 |
| AmCl | | 1.1 | 1.3 | 2.7 |
| AmSul | | 1.0 | 1.3 | 2.7 |
| Am + Lys | | 0.9 | 1.3 | 2.4 |
| Am + EDTA | | 1.6 | 2.8 | 5.2 |
| Am + Tween | | 1.6 | 2.7 | 4.9 |
| Am + Sucrose | | 1.0 | 1.2 | 2.4 |

Figure 3:
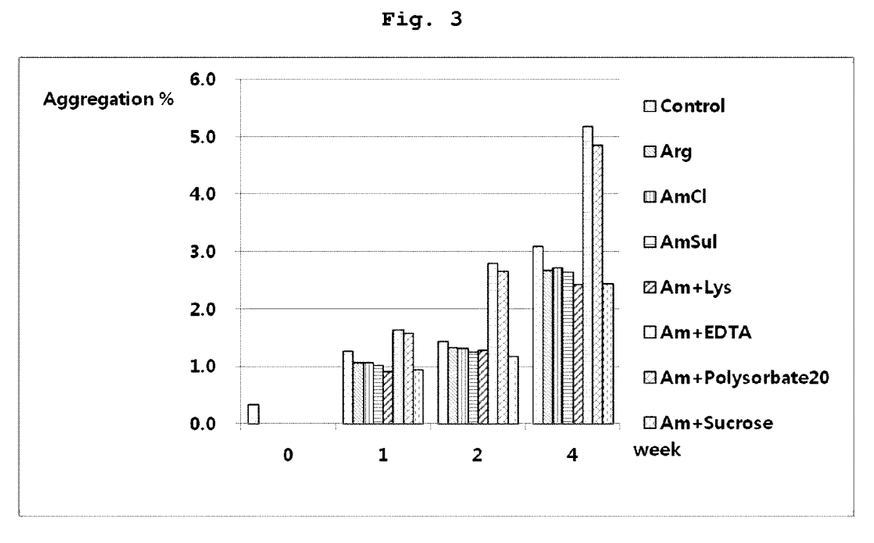
FIG. 3 shows the results of measuring the aggregation degree of etanercept after storing etanercept in formulations containing ammonium chloride at 37° C. for 4 weeks.

TNFR:Fc was stored at 37° C. for 4 weeks, and as a result, it could be seen that the formulations containing the ammonium salt effectively inhibited the aggregation of the protein, and ammonium sulfate also inhibited the aggregation of the protein, similar to ammonium chloride. In addition, interestingly, it could be seen that, when excipients such as EDTA or polysorbate 20 were used in combination with ammonium chloride, the degree of aggregation increased compared to when the negative control formulation was used, but when sucrose and lysine were used in a combination with ammonium chloride, the degree of aggregation decreased when ammonium chloride was used alone (FIG. 3 and Table 1).

Example 4

An experiment was performed to examine the concentration-dependent inhibitory effect of the ammonium chloride excipient proven to have the effect of inhibiting the aggregation of the fusion protein, and was performed at a temperature higher than 37° C. The experiment was performed at a temperature of 45° C. to examine a minute difference in the aggregation of TNFR:Fc.

Specifically, the experiment was performed to examine the effects of combinations of ammonium chloride, ammonium sulfate and other excipients, generally known to have the effect of inhibiting the aggregation of the protein, on the inhibition of aggregation of TNFR:Fc. Specifically, 50 mg/ml TNFR:Fc was stored in a stabilization buffer containing 1% w/v sucrose, 100 mM sodium chloride and 25 mM sodium phosphate (pH 6.4) at 45° C., and then the aggregation inhibitory effect of the ammonium salt in the formulation solution was observed.

A stabilization buffer composition containing no excipient for aggregation inhibition (negative control formulation), a formulation containing 25 mM arginine (positive control formulation), a formulation containing each of 12.5 mM, 25 mM and 50 mM ammonium chloride, a formulation containing 25 mM ammonium chloride and 25 mM lysine or 5% w/v sucrose, and a formulation containing 50 mM ammonium chloride and 25 mM lysine or 5% w/v sucrose were stored at 45° C. for 2 weeks, and then the degree of aggregation was examined. The aggregation inhibitory effect was measured using SE-HPLC in the same manner as described in Example 1.

TABLE 2

Results of measuring the aggregation of etanercept after storing etanercept in formulations containing various concentrations of ammonium chloride at 45° C. for 14 days
% Aggregation

| | Day | | | |
|---|---|---|---|---|
| | 0 | 3 | 7 | 14 |
| control | 0.9 | 2.2 | 3.7 | 4.6 |
| Arg | | 1.9 | 3.2 | 3.8 |
| AmCl 12.5 | | 2.3 | 3.5 | 4.4 |
| AmCl 25 | | 2.1 | 3.2 | 4.0 |
| AmCl50 | | 1.8 | 3.0 | 3.7 |
| AmSul | | 1.7 | 3.0 | 3.6 |
| Am 25 + Lys | | 1.7 | 2.8 | 3.5 |
| Am25 + Suc | | 1.6 | 2.9 | 3.5 |
| Am50 + Lys | | 1.5 | 2.6 | 3.0 |
| Am50 + Suc | | 1.8 | 2.6 | 3.1 |

Figure 4:
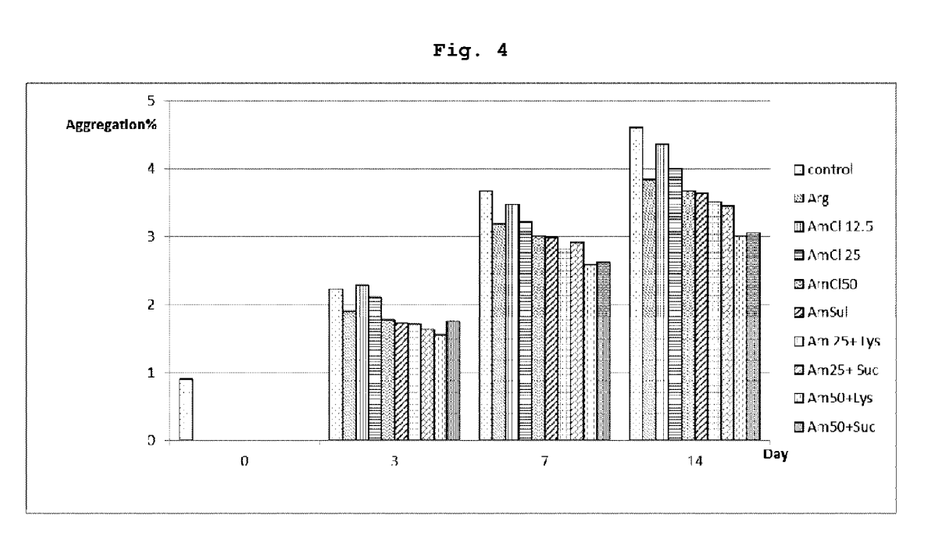
FIGS. 4 and 5 show the results of measuring the aggregation degree of etanercept after storing etanercept in formulation solutions containing arginine, ammonium chloride, ammonium sulfate, ammonium chloride+lysine, ammonium chloride+EDTA, ammonium chloride+polysorbate 20, and ammonium chloride+sucrose at 45° C. for 14 days.
Figure 5:
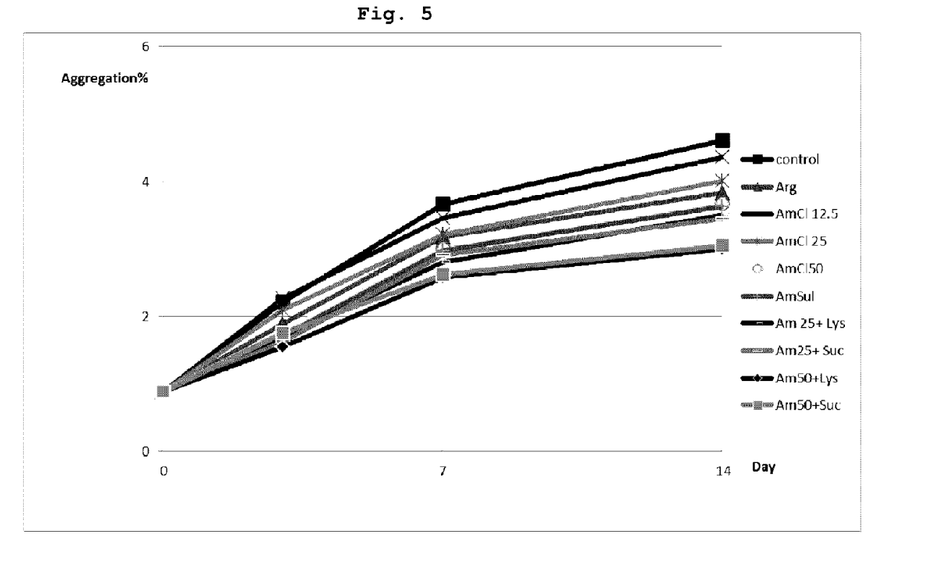

The results of the experiment indicated that the formulation containing the ammonium salt showed an aggregation inhibitory effect equal to or better than the arginine-containing formulation depending on the concentration of the ammonium salt. In addition, it could be seen that, when ammonium chloride or ammonium sulfate was used in a combination with other excipients (lysine and sucrose) generally known to have the effect of inhibiting protein aggregation, a better effect on the inhibition of protein aggregation could be obtained (FIGS. 4 and 5 and Table 2).

Example 5

In this Example, in order to maximize the effect of the ammonium chloride excipient proven to have the effect of inhibiting the aggregation of the fusion protein, formulation solutions prepared using various kinds of buffers were stored at 45° C., and the aggregation inhibitory effects were measured.

Specifically, the experiment was performed to examine the difference in the protein aggregation inhibitory effect between sodium phosphate, sodium succinate, sodium citrate and histidine buffers which are frequently used in protein formulations. 50 mg/ml TNFR:Fc was stored in 100 mM sodium chloride, 50 mM ammonium chloride and 25 mM of each of the above-described four buffers at pH 6.0 and pH 6.5 and at 45° C., and the effect of inhibiting protein aggregation in the formulation solutions was observed.

The aggregation inhibitory effect was measured using SE-HPLC in the same manner as described in Example 1.

From the results of the experiment, it was shown that aggregation in the formulation containing sodium succinate as a buffer was significantly lower than that in the formulations containing other buffers at pH 6.5. Also, aggregation in the formulation containing sodium phosphate buffer that is used in a currently commercially available Enbrel formulation was higher than that in other formulations. In addition, it could be seen that the formulation containing sodium succinate showed a slightly better effect on the inhibition of aggregation compared to the formulations containing other buffers at pH 6.0 (FIG. 6).

Example 6

In this Example, in order to maximize the effect of the sodium succinate buffer having an excellent effect of inhibiting the aggregation of the fusion protein, formulation solutions prepared using sodium succinate buffers adjusted to various pHs were stored at 45° C., and the inhibition of aggregation in the formulation solutions was measured.

Specifically, the experiment was performed to examine a difference in the protein aggregation inhibitory effect between sodium succinate buffers having various pHs. 50 mg/ml TNFR:Fc was stored in 100 mM sodium chloride, 50 mM ammonium chloride and 25 mM sodium succinate buffers at pHs of 6.0, 6.3, 6.5 and 7.0 and at 45° C., and the effect of inhibiting aggregation in the formulation solutions was measured.

The aggregation inhibitory effect was measured using SE-HPLC in the same manner as described in Example 1.

From the results of the experiment, it was shown that the aggregation of the fusion protein decreased as the pH of the sodium succinate buffer decreased, and that the aggregation of the fusion protein in the succinate buffers at pH 6.0 and pH 6.3 was lower than that in the commercially available etanercept formulation (comparative formulation) (FIG. 7).

Example 7

In this Example, in order to confirm that a combination of a sodium succinate buffer having an excellent effect of inhibiting the aggregation of the fusion protein, an ammonium ion component and a basic amino acid has a better effect on the inhibition of aggregation of the fusion protein, a formulation solution prepared by combining components was stored at 45° C., and the effect of inhibiting aggregation in the formulation solution was measured.

Specifically, the experiment was performed to examine the protein aggregation inhibitory effect of a combination of sodium succinate buffer, ammonium chloride and lysine. 50 mg/ml TNFR:Fc was stored in a buffer containing 100 mM sodium chloride, 50 mM ammonium chloride, 25 mM lysine and 25 mM sodium succinate at 45° C., and the effect of inhibiting aggregation in the formulation solution was observed for 0, 5, 10 and 15 days.

The aggregation inhibitory effect was measured using SE-HPLC in the same manner as described in Example 1.

From the results of the experiment, it was shown that aggregation in the composition containing ammonium chloride, succinate and lysine was lower than that in the Enbrel formulation (comparative formulation) (FIG. 8).

INDUSTRIAL APPLICABILITY

As described above, the composition containing an ammonium salt or a combination of an ammonium salt and succinate according to the present invention can effectively inhibit the aggregation of the protein-Fc domain fusion protein, and thus enables the fusion protein to be stored for a long period of time. Accordingly, the composition can be widely used in the medical field that uses the protein-Fc domain fusion protein.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method of stabilizing a protein-Fc domain fusion protein comprising:
   adding an ammonium salt, and succinate at a concentration of 20-30 mM for inhibiting an aggregation of the protein-FC domain fusion protein to a composition comprising the protein-FC domain fusion protein in which the extracellular ligand binding domain of human p75 tumor necrosis factor receptor is fused to the Fc domain of human IgG.

2. The method of claim 1, wherein the succinate is added in the form of a buffer having a pH of 5.5-6.5.

3. The method of claim 1, wherein the ammonium salt is selected from among ammonium chloride, ammonium sulfate, ammonium carbonate, and ammonium nitrate.

4. The method of claim 1, wherein the ammonium salt is comprised at a concentration of 5-500 mM.

5. The method of claim 1, wherein the composition further comprises an excipient.

6. The method of claim 5, wherein the excipient is at least one selected from among basic amino acid, saccharide, and surfactant.

7. The method of claim 6, wherein the excipient is sucrose, lysine or both of sucrose and lysine.

* * * * *